US008217185B2

(12) United States Patent
Kraft

(10) Patent No.: US 8,217,185 B2
(45) Date of Patent: Jul. 10, 2012

(54) MACROCYCLIC LACTONES AS FRAGRANCES

(75) Inventor: Philip Kraft, Duebendorf (CH)

(73) Assignee: Givaudan SA, Vernier (CH)

( * ) Notice: Subject to any disclaimer, the term of this patent is extended or adjusted under 35 U.S.C. 154(b) by 199 days.

(21) Appl. No.: 12/679,846

(22) PCT Filed: Sep. 25, 2008

(86) PCT No.: PCT/CH2008/000396
§ 371 (c)(1),
(2), (4) Date: Mar. 24, 2010

(87) PCT Pub. No.: WO2009/039675
PCT Pub. Date: Apr. 2, 2009

(65) Prior Publication Data
US 2010/0204344 A1  Aug. 12, 2010

(30) Foreign Application Priority Data
Sep. 27, 2007 (GB) .................................. 0718806.3

(51) Int. Cl.
*C07D 313/00* (2006.01)
(52) U.S. Cl. ...................................................... 549/266
(58) Field of Classification Search .................. 549/266
See application file for complete search history.

(56) References Cited

U.S. PATENT DOCUMENTS
| | | |
|---|---|---|
| 5,726,328 A | 3/1998 | Mane |
| 6,255,276 B1 | 7/2001 | Frater |
| 6,284,900 B1 | 9/2001 | Delphis |

FOREIGN PATENT DOCUMENTS
| | | |
|---|---|---|
| DE | 19804673 A1 | 8/1999 |
| EP | 0841333 A1 | 5/1998 |
| EP | 0908455 A | 4/1999 |
| GB | 2423986 A | 9/2006 |
| WO | 9732948 A1 | 9/1997 |
| WO | 03037841 A1 | 5/2003 |

OTHER PUBLICATIONS

XP009110992 "Our Tactics in Ring Enlargement-Construction of Medium and Large Ring Compounds", Totchtermann W. and Kraft P., Synlett, 1996, pp. 1029-1035.

XP002511278 "(4E, 8Z_-12-Methyloxacyclotetradeca-4, 8-died-2-one and Its 7a-Homologue: Comformationally Constrained Double-Unsaturated Macrocyclic Musk by Ring-Closing Alkyne Metathesis" Kraft P. And Berthold C., Synthesis No. 4, 2008, pp. 543-550.

English Language Abstract for DE19804673 taken from esp©cenet.com, Dec. 7, 2006.

English Language Abstract for EP0908455 taken from esp©cenet.com, Apr. 14, 1999.

Ethylidyne Alkynes From Isopropylidene Olefins, S. L. Abidi, Tetrahedron Letters, vol. 27, No. 3, pp. 267-270, 1986.

Our Tactics in Ring Enlargement-Construction of Medium and Large Ring Compounds, Werner Tochtermann and P. Kraft, Institute for Organic Chemistry of University Kiel, 1996.

Schrock Carbyne Catalyst, Walt E. Van Der, University of Pretoria, ed, 2006.

Synthesis of Cyclopentane-Fused Oxygen Heterocycles from the Intramolecular Reaction of Alkynes with Cyclopropylcarbene-Chromium Complexes, James W. Herndon and J. Matasi, Department of Chemistry and Biochemistry, University of Maryland, pp. 786-788, 1989.

Improvement on the Synthesis of (E)-alk-3-enoic Acids, Nikitas Ragoussis and V. Ragoussis, Vioryl S.A. Research Department, University of Athens, Greece, 1998.

Synthese and Olfaktorische Eigenschaften von Pentadecen-und Pentadecadienoliden, zur Erlangung des Doktorgades der Mathematisch-Naturwissenschftlichen Fakulat, Kiel, 1996.

Access to C-15 Macrocyclic Ketones by Ineravtive Fragmentations of a Tricyclic System, Dr. C. Fehr, J. Galindo et al., Angew Chem. Int. Ed. 2002, 21, No. 23, 2002.

*Primary Examiner* — Nizal Chandrakumar
(74) *Attorney, Agent, or Firm* — Norris McLaughlin & Marcus PA

(57) ABSTRACT

The present invention refers to methyl-substituted double-unsaturated macrocyclic lactones comprising 14 to 17 ring atoms of formula (I)

wherein n and m are independently selected from 1, 2, 3 and 4 with the proviso that $3 \leq n+m \leq 6$. The invention relates furthermore to their use as odorant and fragrance composition comprising them.

6 Claims, No Drawings

MACROCYCLIC LACTONES AS FRAGRANCES

This is an application filed under 35 USC 371 of PCT/CH2008/000396.

The present invention refers to methyl-substituted double-unsaturated macrocyclic lactones comprising 14 to 17 ring atoms. The invention relates furthermore to their use as odorants and fragrance composition comprising them.

Musk odorants are indispensable in perfumery to confer aspects of sensuality that distinguishes a perfume from being merely a floral bouquet or potpourri, and they often make up more than 10% by weight of a perfume formula and thereby decisively influence the overall character of a fragrance. Therefore there is a constant demand for new, unique musk odorants that convey a signature to a fragrance with specific harmonic side notes. These side notes should best blend well with the floral heart of a composition and extend it into the foundation of a fragrance. Therefore floral side notes with a warm, sweet-herbaceous, aromatic character are most ideally suited. To have an impact on the overall composition, these signature musks should in addition be diffusive and powerful.

Macrocycles constitute the only class of musks that occurs in nature. Despite a relatively high price, their authenticity and natural character makes them highly appreciated in perfumery. Whereas most macrocyclic musks are saturated or contain only one double bond, only three double-unsaturated unsubstituted macrocyclic musks are known, namely the isomeric (4E/Z)-mixture of (4E/Z,8E)-oxacyclohexadeca-4,8-dien-2-one with a strong, very erogenous-animalic, natural musk odour with sweet, warm sandalwood accents (W. Tochtermann, P. Kraft, *Synlett* 1996, 1029), the isomeric (3E/Z)-mixture of (3E/Z,8E)-oxacyclohexadeca-3,8-dien-2-one with a musk odour accompanied by unpleasant pear- and mushroom-like undertones (G. Bunte, *PhD Thesis*, Christian-Albrechts-Universität zu Kiel, 1996, 106-108), and (6Z,10Z)-cyclopentadeca-6,10-dienone with a greasy, waxy, relatively weak musk odour (C. Fehr, J. Galindo, O. Etter, W. Thommen, *Angew. Chem. Int. Ed.* 2002, 41, 4523).

Surprisingly we found a new class of compounds possessing musk characteristics of high diffusion and strength, with desirable specific floral side notes of warm, sweet-herbaceous, aromatic character.

Thus the present invention refers in one aspect to a compound of formula (I)

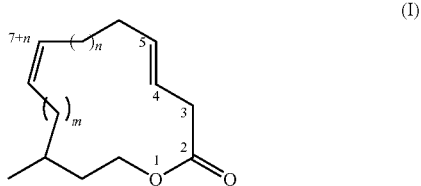

(I)

wherein n and m are independently selected from 1, 2, 3 and 4 with the proviso that $3 \leq n+m \leq 6$, e.g. n+m is 4 or 5; and the double bond between C-4 and C-5 is in (E)-configuration and the bond between C-(7+n) and C-(8+n) is in (Z)-configuration.

The compounds according to the present invention comprise one chiral centre and as such exist as racemic or enantiomerically-enriched mixtures of enantiomers. Resolving stereoisomers or employing chiral starting material adds however to the cost of these odorants, so it is preferred to use the compounds as racemic mixtures simply for economic reasons. However, if it is desired to prepare individual stereoisomers, this may be achieved according to methodology known in the art, e.g. preparative HPLC and GC on chiral stationary phases, by stereoselective synthesis, or starting from available chiral raw materials, such as optically active citronellol.

The compounds of formula (I) wherein m is 1 and n is 2 or 3, and compounds wherein m is 2 and n is selected from 1, 2, 3 and 4 represent a particular aspect of the invention.

In a particular embodiment compounds of formula (I) are selected from (4E,9Z)-13-methyloxacyclopentadeca-4,9-dien-2-one, (4E,8Z)-12-methyloxacyclotetradeca-4,8-dien-2-one, (4E,10Z)-13-methyloxa-cyclopentadeca-4,10-dien-2-one, (4E,10Z)-14-methyloxacyclohexadeca-4,10-dien-2-one, (4E,11Z)-15-methyloxacycloheptadeca-4,11-dien-2-one, and (4E,9Z)-12-methyloxacyclo-tetradeca-4,9-dien-2-one, and mixtures thereof.

Amongst the compounds of the invention, (4E,9Z)-13-methyloxacyclopentadeca-4,9-dien-2-one may be cited as a typical representative. It emanates an intense, pleasant sweet aromatic-powdery musk odour with floral facets in the direction of jasmin and slightly green aspects. When the odour of this compound is compared with the one of the closest prior art compound, namely (4E/Z,8E)-oxacyclohexadeca-4,8-dien-2-one, which possesses a strong, very erogenous-animalic, natural musk odour with sweet, warm sandalwood accents, then the sandalwood, woody aspects of the latter one are completely missing in (4E,9Z)-13-methyloxacyclopentadeca-4,9-dien-2-one, as is also any animalic connotation. In contrary to (4E/Z,8E)-oxacyclohexadeca-4,8-dien-2-one, the musk character of (4E,9Z)-13-methyloxacyclopentadeca-4,9-dien-2-one is floral-jasminic, and also the sweet aromatic, and green herbaceous facets are otherwise only common in the floral family. The floral and warm-herbaceous facets are also characteristic for the musk odour of the (4E,8Z)-12-methyloxacyclotetradeca-4,8-dien-2-one which shows in addition a metallic, hot-iron inclination. This metallic, hot-iron inclination appears also in other macrocyclic musks, such as Habanolide (oxacyclohexadec-12/13-en-2-one), but never in a floral context. Therefore, the compounds of the formula (I) possess different and unexpected odours from the ones of their prior art closest structural analogues.

The compounds of the present invention may be used alone, as mixtures thereof, or in combination with a base material. As used herein, the "base material" includes all known odorant molecules selected from the extensive range of natural and synthetic molecules currently available, such as ethereal oils and extracts, alcohols, aldehydes and ketones, ethers and acetals, esters and lactones, macrocycles and heterocyles, and/or in admixture with one or more ingredients or excipients conventionally used in conjunction with odorants in fragrance compositions, for example, carrier materials, and other auxiliary agents commonly used in the art, e.g. a diluent conventionally used in conjunction with odorants, such as dipropylene glycol (DPG), isopropyl myristate (IPM), and triethyl citrate (TEC) and alcohol (e.g. ethanol). The use of a compound of formula (I) in is neither limited to any particular perfume type nor to any special olfactory direction, odourant or class of substance. Thus, compounds of the general formula may be mixed with, for example, ethereal oils and extracts, e.g. castoreum, costus root oil, oak moss absolute, geranium oil, jasmine absolute, patchouli oil, rose oil, sandalwood oil or ylang-ylang oil;
  alcohols, e.g. citronellol, Ebanol® (3-methyl-5-(2,2,3-trimethyl-3-cyclopenten-1-yl-4-penten-2-ol), eugenol, geraniol, Super Muguet (6-ethyl-3-methyl-6-octen-1-ol), linalool, phenylethyl alcohol, Sandalore® (5-(2,2,3- trimethyl-3-cyclopentenyl)-3-methylpentan-2-ol), terpineol or Timberol® [1-(2,2,6-trimethylcyclohexyl)hexan-3-ol);

aldehydes and ketones, e.g. Azurone [7-(3-methylbutyl)-2H-1,5-benzodioxepin-3(4H)-one], α-amylcinnamaldehyde, hydroxycitronellal, Iso E Super [1-(2,3,8,8-tetramethyl-1,2,3,4,5,6,7,8-octahydronaphthalen-2-yl)ethanone], Isoraldeine, Hedione® [methyl (3-oxo-2-pentylcyclopentyl)acetate], maltol, methyl cedryl ketone, methyl ionone, Pomarose [(2E)-5,6,7-trimethylocta-2,5-dien-4-one] or vanillin;

ethers and acetals, e.g. Ambrox® (3a,6,6,9a-tetramethyldodecahydronaphtho[2,1-b]furan), geranyl methyl ether, rose oxide or Spirambrene (2,2,3',7',7'-pentamethylspiro(1,3-dioxan-5,2'-norcarane));

esters and lactones, e.g. benzyl acetate, cedryl acetate, γ-decalactone, Hevetolide® (2-[1-(3,3-dimethylcyclohexyl)ethoxy]-2-methylpropan-1-ol propanoate), Serenolide (2-[1-(3,3-dimethylcyclohexyl)ethoxy]-2-methylpropan-1-ol cyclopropanecarboxylate), γ-undecalactone or vetivenyl acetate;

macrocycles, e.g. ambrettolide, ethylene brassylate or Exaltolide® (oxacyclohexadecan-2-one); and heterocycles, e.g. isobutylchinoline.

However, due to their unique musk character, the compounds of the present invention are especially well suited for use in combination with more pronounced floral heart notes, both in feminine and masculine fragrances.

The compounds of the present invention may be used in a broad range of fragrance applications, e.g. in any field of fine and functional perfumery, such as perfumes, household products, laundry products, body care products and cosmetics. The compounds can be employed in widely varying amounts, depending upon the specific application and on the nature and quantity of other fragrances. The proportions in which the compounds of the present invention are employed may vary within a large range of values and will depend upon the nature of the applications one intends to perfume, for example the nature of co-ingredients. It also depends on the particular effect that the perfumer seeks. Generally however, one may employ up to about 35% by weight of a compound of formula (I), or a mixture thereof in perfumes, e.g. from about 5% by weight to about 30% by weight, and up to about 15% by weight based on the perfume composition when admixed to other products, e.g. laundry products. However, these values are given only by way of example, since the experienced perfumer may also achieve effects or may create novel accords with lower or higher concentrations.

The compounds of the present invention may be employed into a consumer product base simply by directly mixing a compound of formula (I), a mixture thereof, or a by admixing a fragrance composition with the consumer product base, or they may, in an earlier step, be entrapped with an entrapment material such as polymers, capsules, microcapsules and nanocapsules, liposomes, film formers, absorbents such as carbon or zeolites, cyclic oligosaccharides and mixtures thereof, and/or they may be chemically bonded to substrates, which are adapted to release the fragrance molecule of the present invention upon application of an external stimulus such as light, enzymes, or the like, and then mixed with the consumer product base.

Thus, the invention additionally provides a method of manufacturing a fragrance application, comprising the incorporation of a compound of formula (I), as a fragrance ingredient, either by directly admixing the compound to the consumer product base or by admixing a fragrance composition comprising a compound of formula (I) or a precursor thereof, which may then be mixed with a consumer product base, using conventional techniques and methods. Through the addition of an olfactory acceptable amount of a compound of the present invention, or a mixture thereof, the odour notes of a consumer product base will be improved, enhanced and/or modified.

By "precursor" is meant, in particular, an addition product with one or both of the double bonds of a compound of formula (I), which would cleave for instance after oxidation, enzymatic reaction, heating or treatment with a base in the application, thereby releasing a double-unsaturated macrocyclic lactone of formula (I). Suitable reactions and corresponding substrates comprise all kind of eliminations in which C═C double-bonds are formed, such as the hydro-tosyloxy-elimination, the hydro-dialkyloxyammonio-elimination, Hofmann degradation or the Chugaev or Shapiro reaction. Specifically, the ([7+n]Z)-configured double-bond can be advantageously generated in a Ramberg-Bäcklund reaction from a corresponding α-halosulfone.

Thus, the invention furthermore provides a method for improving, enhancing and/or modifying a fragrance application through the addition thereto of an olfactory acceptable amount of a compound of formula (I), or a mixture thereof.

The invention also provides a fragrance application comprising:
a) a compound of formula (I), or a mixture thereof; and
b) a consumer product base.

As used herein, "consumer product base" means a composition for use as a consumer product to fulfill specific actions, such as cleaning, softening, and caring or the like. Examples of such products include fine perfumery, e.g. perfume and eau de toilette; fabric care, household products and personal care products such as laundry care detergents, rinse conditioner, personal cleansing composition, detergent for dishwasher, surface cleaner; laundry products, e.g. softener, bleach, detergent; body care products, e.g. shampoo, shower gel; air care products and cosmetics, e.g. deodorant, and vanishing creme. This list of products is given by way of illustration and is not to be regarded as being in any way limiting.

The compounds of the formula (I) may be prepared by alkyne metathesis of the corresponding (3E)-3'-methylalk-[4+m]'-ynyl alk-3-en-[6+n]-ynoates (i.e. a compound of the formula (II)

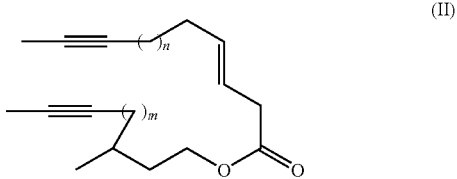

(II)

wherein n and m are independently selected from 1, 2, 3 and 4 with the proviso that 3≦n+m≦6, e.g. n+m is 4 or 5) in the presence of Schrock's carbyne catalyst [Me₃CC≡W(OtBu)₃] or other alkyne metathesis catalysts.

Surprisingly, it was found that the alkyne metathesis does not compete with an enyne metathesis in the case of the respective substrates as would have been expected and thus constitutes a further aspect of the present invention. The (3E)-3'-methylalk-[4+m]'-ynyl alk-3-en-[6+n]-ynoates of the formula (II) may conveniently be prepared by common esterification reactions of the alk-3-en-[6+n]-ynoic acids with (3E)-3'-methylalk-[4+m]'-ynols, e.g. Steglich esterification employing 4-(dimethylamino)-pyridine and N,N'-dicyclohexylcarbodiimide as catalysts under conditions known to the person skilled in the art. The alk-3-en-[6+n]-ynoic acids are accessible by β,γ-selective Knoevenagel reaction as described e.g. by N. Ragoussis et al. (in *J. Chem. Soc., Perkin Trans.* 1, 1998, 3529) from the corresponding alk-[4+n]-yne aldehydes in the presence of piperidinium acetate, while for the preparation of (3E)-3'-methylalk-[4+m]'-ynols several methods are known in the literature, including the nitrous acid-induced demethylation of the isopropylidene group of citronellol for the synthesis of 3-methyloct-6-yn-1-ol (S. L. Abidi, *Tetrahedron Lett.* 1986, 27, 267) and Corey-Fuchs reactions of protected hydroxy aldehydes. The alk-[4+n]-yne aldehydes required for the synthesis of the alk-3-en-[6+n]-ynoic acids may be prepared by Eschenmoser-Ohloff reaction of 2-methyl-substituted cycloalk-2-enones after Weitz-Scheffer epoxidation or by methylation of terminal alkynols according to the procedure of Herndon et al. (J. Yan, J. Zhu, J. J. Matasi, J. W. Herndon, *J. Org. Chem.* 1990, 55, 786).

The invention is now further described with reference to the following non-limiting examples. These examples are for the purpose of illustration only and it is understood that variations and modifications can be made by one skilled in the art. The NMR data are given relative to internal $SiMe_4$ standard.

EXAMPLE 1

(4E,9Z)-13-methyloxacyclopentadeca-4,9-dien-2-one

Oct-6-ynal was synthesized according to the synthetic scheme of J. Yan, J. Zhu, J. J. Matasi, J. W. Herndon, *J. Org. Chem.* 1990, 55, 786 with additional THP-protection during the methylation step. Commercially available hex-5-yn-1-ol (15.2 g, 155 mmol) was protected (DHP, PTSA, $CH_2Cl_2$, 0° C.→room temp., 5 h), and subsequently methylated (1.6M BuLi, MeI, THF, –78° C.→room temp., 12 h). Cleavage of the THP ether (PPTS, MeOH, room temp., 12 h) afforded hept-5-yn-1-ol (10.6 g, 61%), which was mesylated (MsCl, $Et_3N$, $Et_2O$, 0° C.→room temp., 12 h) and subsequently cyanated (KCN, DMF, reflux, 3.5 h) to provide oct-6-yne nitrile (7.90 g, 69%). Reduction of this nitrile (DIBAL-H, THF, 0° C.→room temp., 12 h) furnished oct-6-ynal (6.70 g, 83%).

At room temp., a piperidinium acetate solution, freshly prepared by mixing piperidine (110 μL, 1.10 mmol) and acetic acid (65.0 μL, 1.10 mmol) in dimethyl sulfoxide (5.00 mL), was injected into a stirred solution of the prepared oct-6-ynal (6.70 g, 54.0 mmol) and malonic acid (11.2 g, 108 mmol) in dimethyl sulfoxide (200 mL). After refluxing the reaction mixture for 4 h, water (50 mL) and ether (100 mL) were added at room temp., and the layers were separated. The aqueous layer was extracted with ether (3×100 mL), and the combined organic extracts were washed with water (100 mL), dried ($Na_2SO_4$), and concentrated under reduced pressure. The crude material (GC, $\Delta^3$:$\Delta^2$=70:30) was purified by chromatography on silica gel [200 g; pentane-$Et_2O$ (4:1); $R_f$=0.24 in pentane-$Et_2O$ (5:1)] and subsequent Kugelrohr distillation at 160° C./13 mbar to afford (3E)-dec-3-en-8-ynoic acid (3.79 g, 42%) as a colourless crystalline solid (mp, 40-43° C.).

IR (neat): ν 2937, 2860 (O—H), 1689 (C=O), 1347 ($CH_3$), 964 (C=C, trans) $cm^{-1}$.

$^1$H NMR ($CDCl_3$): δ 1.56 (quint, J=7.0 Hz, 2 H, 6-$H_2$), 1.78 (t, J=2.5 Hz, 3 H, 10-$H_3$), 1.99-2.18 (m, 4 H, 5-, 7-$H_2$), 3.08 (td, J=1.0, 6.0 Hz, 2 H, 2-$H_2$), 5.50-5.63 (m, 2 H, 3-, 4-H), 11.34 (br. s, 1 H, OH).

$^{13}$C NMR ($CDCl_3$): δ 3.4 (q, C-10), 18.1 (t, C-7), 28.3 (t, C-6), 31.5 (t, C-5), 37.8 (t, C-2), 75.7 (s, C-9), 78.8 (s, C-8), 121.5 (d, C-3), 134.4 (d, C-4), 178.8 (s, C-1).

MS: m/z (%) 41 (100) [$C_3H_5^+$], 45 (24) [$CO_2H^+$], 53 (68) [$C_4H_5^+$], 60 (7) [$CH_3CO_2H^+$], 66 (39) [$C_5H_6^+$], 70 (40) [$C_5H_{10}^+$], 93 (68) [$C_7H_9^+$], 106 (59) [$M^+$-$CH_3CO_2H$], 112 (9) [$C_6H_8O_2^+$], 121 (28) [$M^+$-$CO_2H$], 133 (3) [$M^+$-$H_2O$—$CH_3$], 138 (2) [$M^+$-$C_2H_4$], 147 (1) [$M^+$-H—$H_2O$], 151 (5) [$M^+$-$CH_3$], 165 (2) [$M^+$-H], 166 (1) [$M^+$].

At room temp., 4-(dimethylamino)pyridine (122 mg, 0.999 mmol) was added to a stirred solution of (3E)-dec-3-en-8-ynoic acid (1.66 g, 9.99 mmol), and 3-methyloct-6-yn-1-ol (1.40 g, 9.99 mmol) in ether (30 mL). 3-Methyloct-6-yn-1-ol (1.80 g, 26%) was prepared from citronellol (7.81 g, 50.0 mmol) and sodium nitrite (93.2 g, 135 mmol) in acetic acid/water (5:2, 210 mL) according to the procedure of S. L. Abidi, *Tetrahedron Lett.* 1986, 27, 267. At 0° C., N,N'-dicyclohexylcarbodiimide (2.27 g, 11.0 mmol) was added, and the reaction mixture was stirred for 10 min at this temp., upon which a colorless precipitate formed. This insoluble material was filtered off with suction in a sintered funnel, and the filtrate was concentrated under reduced pressure. Chromatography of the resulting residue on silica gel [50 g; pentane-$Et_2O$ (20:1); $R_f$=0.50 in pentane-$Et_2O$ (10:1)] afforded (3E)-3'-methyloct-6'-ynyl dec-3-en-8-ynoate (1.34 g, 47%) as a colourless liquid.

IR (neat): ν 1735 (OC=O), 968 (C=C, trans) $cm^{-1}$.

$^1$H NMR ($C_6D_6$): δ 0.49 (d, J=7.0 Hz, 3 H, 3'-Me), 1.17 ($m_c$, 1 H, 4'-$H_b$), 1.20 ($m_c$, 1 H, 2'-$H_b$), 1.40 ($m_c$, 1 H, 4'-$H_a$), 1.44 ($m_c$, 1 H, 2'-$H_a$), 1.46 (quint, J=7.0 Hz, 2 H, 6-$H_2$), 1.55 (t, J=2.5 Hz, 3 H, 8'-$H_3$), 1.56 ($m_c$, 1 H, 3'-H), 1.57 (t, J=2.5 Hz, 3 H, 10-$H_3$), 1.99 ($m_c$, 2 H, 5-$H_2$), 2.02 ($m_c$, 2 H, 5'-$H_2$), 2.04 ($m_c$, 2 H, 7-$H_2$), 2.86 (dd, J=1.0, 7.0 Hz, 2 H, 2-$H_2$), 4.01 ($m_c$, 2 H, 1'-$H_2$), 5.31 (ttd, J=1.0, 7.0, 15.5 Hz, 1 H, 4-H), 5.61 (ttd, J=1.0, 7.0, 15.5 Hz, 1 H, 3-H).

$^{13}$C NMR ($C_6D_6$): δ 3.3 (q, C-10), 3.4 (q, C-8'), 16.7 (t, C-7), 18.4 (t, C-5'), 18.9 (q, 3'-Me), 28.8 (t, C-6), 29.3 (d, C-3'), 31.8 (t, C-5), 35.4 (t, C-2'), 36.3 (t, C-4'), 38.3 (t, C-2), 62.8 (t, C-1'), 75.6 (s, C-7'), 75.8 (s, C-9), 79.1 (s, C-8), 79.2 (s, C-6'), 123.2 (d, C-3), 133.5 (d, C-4), 171.2 (s, C-1).

MS: m/z (%) 41 (80) [$C_3H_5^+$], 55 (80) [$C_4H_7^+$], 60 (1) [$CH_3CO_2H^+$], 67 (69) [$C_5H_7^+$], 81 (100) [$C_6H_9^+$], 93 (59) [$C_7H_9^+$], 121 (44) [$C_9H_{13}^+$], 124 (34) [$C_{10}H_{14}O_2^+$—$C_3H_6$], 149 (7) [$C_{10}H_{13}O^+$], 166 (7) [$C_{10}H_{14}O_2^+$], 273 (1) [$M^+$-$CH_3$]. $C_{19}H_{28}O_2$ (288.43): calcd. C 79.12, H 9.78; found C 79.13, H 9.77.

A solution of (3E)-3'-methyloct-6'-ynyl dec-3-en-8-ynoate (435 mg, 1.51 mmol) in absolute chlorobenzene (80 mL) was degassed with argon for 15 min, prior to the addition of Schrock's carbyne catalyst ($Me_3CC\equiv W(OtBu)_3$, 71.3 mg, 0.151 mmol). With a slow flow of argon, the resulting mixture was refluxed for 24 h and then allowed to cool down to room temp. The solvent was removed under reduced pressure, and the resulting residue was purified by chromatography on silica gel [50 g; pentane-$Et_2O$ (50:1); $R_f$=0.44 in pentane-$Et_2O$ (5:1)] to provide (4E)-13-methyloxacyclo-pentadec-4-en-9-yn-2-one (150 mg, 42%) as a colourless liquid.

IR (neat): 1733 (OC=O), 968 (C=C, trans) $cm^{-1}$.

$^1$H NMR ($CDCl_3$): δ 0.92 (d, J=6.5 Hz, 3 H, 13-Me), 1.24 ($m_c$, 1 H, 12-$H_b$), 1.35 ($m_c$, 1 H, 14-$H_b$), 1.41-1.61 (m, 3 H, 7-$H_2$, 12-$H_a$), 1.72 (ttd, J=3.5, 10.5, 14.5 Hz, 1 H, 14-$H_a$), 1.93 ($m_c$, 1 H, 13-H), 2.09-2.31 (m, 6 H, 6-, 8-, 11-$H_2$), 3.03 (ddd, J=1.0, 2.5, 6.5 Hz, 2 H, 3-$H_2$), 4.19 (dd, J=3.5, 10.5 Hz, 1 H, 15-$H_b$), 4.23 (dd, J=3.5, 10.5 Hz, 1 H, 15-$H_a$), 5.50 (ttd, J=1.5, 7.0, 15.0 Hz, 1 H, 5-H), 5.67 (ttd, J=1.5, 7.0, 15.0 Hz, 1 H, 4-H).

$^{13}$C NMR (CDCl$_3$): δ 16.4 (t, C-11), 17.0 (t, C-8), 18.5 (q, 13-Me), 25.5 (t, C-7), 26.7 (d, C-13), 30.3 (t, C-6), 35.7 (t, C-14), 35.9 (t, C-12), 39.0 (t, C-3), 62.0 (t, C-15), 79.7 (s, C-10), 80.2 (s, C-9), 123.8 (d, C-4), 132.5 (d, C-5), 171.7 (s, C-2).

MS: m/z (%) 41 (91) [C$_3$H$_5$$^+$], 60 (1) [CH$_3$CO$_2$H$^+$], 91 (100) [C$_7$H$_7$$^+$], 99 (6) [C$_7$H$_{15}$$^+$], 178 (11) [O$_{13}$H$_{22}$$^+$], 192 (66) [M$^+$-C$_2$H$_2$O], 206 (16) [M$^+$-CO], 219 (2) [M$^+$-CH$_3$], 234 (1) [M$^+$].

Quinoline (4.86 μL, 0.0411 mmol) and 10% Pd/BaSO$_4$ (0.88 mg, 0.00824 mmol) were added to a stirred solution of (4E)-13-methyloxacyclopentadec-4-en-9-yn-2-one (48.2 mg, 0.206 mmol) in ethanol (2.0 mL). The reaction flask was flushed with argon followed by hydrogen, and the reaction mixture was stirred under hydrogen atmosphere at room temp. and ambient pressure. After 3.5 h, GC-monitoring indicated complete conversion, upon which the catalyst was filtered off through a pad of Celite and washed with ethanol. The solvent was removed under reduced pressure, and the resulting residue purified by chromatography on silica gel [20 g; pentane-Et$_2$O (10:1); R$_f$=0.78 in pentane-Et$_2$O (5:1)] to furnish (4E,9Z)-13-methyloxacyclopentadeca-4,9-dien-2-one (44.8 mg, 92%) as a colourless odoriferous liquid.

IR (neat): ν 1733 (O—C═O), 968 (C═C, trans), 696 (C═C, cis) cm$^{-1}$.

$^1$H NMR (CDCl$_3$): δ 0.92 (d, J=6.5 Hz, 3 H, 13-Me), 1.20-1.44 (m, 2 H, 12-, 14-H$_b$), 1.46-1.63 (m, 3 H, 7-H$_2$, 12-H$_a$), 1.72 (m$_c$, 1 H, 14-H$_a$), 1.95-2.12 (m, 7 H, 6-, 8-, 11-H$_2$, 13-H), 3.03 (ddd, J=1.0, 1.0, 6.5 Hz, 2 H, 3-H$_2$), 4.12 (ddd, J=3.0, 9.5, 11.5 Hz, 1 H, 15-H$_b$), 4.21 (ddd, J=3.0, 6.0, 11.5 Hz, 1 H, 15-H$_a$), 5.28 (ttd, J=1.0, 6.5, 11.0 Hz, 1 H, 5-H), 5.38 (ttd, J=1.0, 6.5, 11.0 Hz, 1 H, 4-H), 5.41-5.53 (m, 2 H, 9-, 10-H).

$^{13}$C NMR (CDCl$_3$): δ 20.7 (q, 13-Me), 24.2 (t, C-11), 25.6 (t, C-7), 27.4 (t, C-8), 29.9 (d, C-13), 30.1 (t, C-6), 34.8 (t, C-14), 36.5 (t, C-12), 39.2 (t, C-3), 62.9 (t, C-15), 123.1 (d, C-4), 129.7 (d, C-9), 130.8 (d, C-5), 133.9 (d, C-10), 172.0 (s, C-2).

MS: m/z (%) 41 (72) [C$_3$H$_5$$^+$], 60 (2) [CH$_3$CO$_2$H$^+$], 67 (89) [C$_5$H$_7$$^+$], 81 (100) [C$_6$H$_9$$^+$], 176 (5) [M$^+$-CH$_3$COOH], 203 (1) [M$^+$-H$_2$O—CH$_3$], 208 (1) [M$^+$-CO], 218 (1) [M$^+$-H$_2$O], 236 (2) [M$^+$].

C$_{15}$H$_{24}$O$_2$ (236.35): calcd. C 76.23, H 10.23; found C 76.30, H 10.30.

Odour description: intense, pleasant sweet aromatic-powdery musk odour with floral facets in the direction of jasmin and slightly green aspects.

EXAMPLE 2

(4E,8Z)-12-Methyloxacyclotetradeca-4,8-dien-2-one

At room temp., 2N aqueous sodium hydroxide (7.00 mL, 14.0 mmol), followed by 30% aqueous hydrogen peroxide (11.0 mL, 112 mmol) was added to a stirred solution of commercially available 2-methylcyclohex-2-enone (2.20 g, 20.0 mmol) in methanol (250 mL), upon which the resulting red color of the solution faded within 10 min. After stirring at room temp. for 24 h, the reaction mixture was diluted with water (200 mL) and extracted with dichloromethane (3×150 mL). The combined organic extracts were washed with water (200 mL) and dried with sodium sulfate. The solvent was removed under reduced pressure, and the resulting residue purified by chromatography on silica gel [40 g; pentane-Et$_2$O (9:1); R$_f$=0.29] to furnish 1-methyl-7-oxabicyclo[4.1.0]heptan-2-one (1.18 g, 47%) as a colourless liquid.

At −10° C. p-toluene sulfonylhydrazine (6.14 g, 33.0 mmol) was added portionwise to a stirred solution of 1-methyl-7-oxabicyclo[4.1.0]heptan-2-one (3.78 g, 30.0 mmol) in acetic acid/dichloromethane (1:1, 80 mL). The reaction mixture was allowed to warm up slowly by not renewing the cooling medium, and at 10° C., GC-monitoring indicated complete conversion. Crushed ice (20 g) was added and the layers were separated. The aqueous layer was extracted with dichloromethane (2×50 mL), and the combined organic solutions were neutralized with ice-cold saturated aqueous sodium bicarbonate. After drying with sodium sulfate and removal of the solvent under reduced pressure, chromatography of the resulting residue on silica gel [50 g; pentane-Et$_2$O-Et$_3$N (3:1:0.01); R$_f$=0.48 in pentane-Et$_2$O (5:1)] afforded hept-5-ynal (1.74 g, 53%) as a colourless liquid.

At room temp., a piperidinium acetate solution, freshly prepared by mixing piperidine (35.0 μL, 0.354 mmol) and acetic acid (19.0 μL, 0.332 mmol) in dimethyl sulfoxide (1.00 mL), was injected into a stirred solution of the prepared hept-5-ynal (1.50 g, 13.6 mmol) and malonic acid (2.83 g, 27.2 mmol) in dimethyl sulfoxide (50 mL). After refluxing the reaction mixture for 4 h, water (10 mL) and ether (20 mL) were added at room temp., and the layers were separated. The aqueous layer was extracted with ether (3×25 mL), and the combined organic extracts were washed with water (25 mL), dried (Na$_2$SO$_4$), and concentrated under reduced pressure. Kugelrohr distillation at 149° C./14 mbar furnished (3E)-non-3-en-7-ynoic acid (902 mg, 44%) as colorless crystals (mp 43-45° C.).

IR (neat): ν 2916 (O—H), 1691 (C═O), 1335 (CH$_3$), 969 (C═C, trans) cm$^{-1}$.

$^1$H NMR (CDCl$_3$): δ 1.77 (t, J=2.5 Hz, 3H, 9-H$_3$), 2.18-2.24 (m, 4 H, 5-, 6-H$_2$), 3.10 (dd, J=1.0, 6.0 Hz, 2 H, 2-H$_2$), 5.54-5.70 (m, 2 H, 3-, 4-H), 11.36 (br. s, 1 H, OH) ppm.

$^{13}$C NMR (CDCl$_3$): δ 3.4 (q, C-9), 18.8 (t, C-6), 32.0 (t, C-5), 37.7 (t, C-2), 76.1 (s, C-8), 78.3 (s, C-7), 122.0 (d, C-3), 133.6 (d, C-4), 178.5 (s, C-1) ppm. —MS: m/z (%) 45 (20) [CO$_2$H$^+$], 53 (100) [C$_4$H$_5$$^+$], 57 (89) [C$_4$H$_9$$^+$], 60 (7) [CH$_3$CO$_2$H$^+$], 79 (33) [C$_6$H$_7$$^+$], 92 (42) [M$^+$-CH$_3$CO$_2$H], 93 (97) [M$^+$-CH$_3$CO$_2$], 99 (3) [M$^+$-C$_4$H$_5$], 107 (68) [M$^+$-CO$_2$H], 124 (2) [M$^+$-CO], 137 (3) [M$^+$-CH$_3$], 151 (7) [M$^+$-H], 152 (1) [M$^+$].

At room temp., 4-(dimethylamino)pyridine (68.4 mg, 0.559 mmol) was added to a stirred solution of (3E)-non-3-en-7-ynoic acid (850 mg, 5.59 mmol) and 3-methyloct-6-yn-1-ol (790 mg, 5.59 mmol) in ether (20 mL). 3-Methyloct-6-yn-1-ol (1.80 g, 26%) was prepared from citronellol (7.81 g, 50.0 mmol) and sodium nitrite (93.2 g, 135 mmol) in acetic acid/water (5:2, 210 mL) according to the procedure of S. L. Abidi, *Tetrahedron Lett.* 1986, 27, 267. At 0° C., N,N'-dicyclohexylcarbodiimide (1.27 g, 6.14 mmol) was added, and the reaction mixture was stirred for 5 min at this temp., upon which a colorless precipitate formed. This insoluble material was filtered off with suction in a sintered funnel, and the filtrate was concentrated under reduced pressure. Chromatography of the resulting residue on silica gel [50 g; pentane-Et$_2$O (20:1); R$_f$=0.65 in pentane-Et$_2$O (5:1)] afforded (3E)-3'-methyloct-6'-ynyl non-3-en-7-ynoate (470 mg, 31%) as a colourless liquid.

IR (neat): ν 1734 (O—C═O), 967 (C═C, trans) cm$^{-1}$.

$^1$H NMR (C$_6$D$_6$): δ 0.70 (d, J=6.5 Hz, 3 H, 3'-Me), 1.14-1.26 (m, 2 H, 2'-, 4'-H$_b$), 1.36-1.52 (m, 2 H, 2'-, 4'-H$_a$), 1.55 (m$_c$, 1 H, 3'-H), 1.56 (t, J=2.5 Hz, 3 H, 8'-H$_3$), 1.59 (t, J=2.5 Hz, 3 H, 9-H$_3$), 1.97-2.14 (m, 6 H, 5-, 5'-, 6'-H$_2$), 2.88 (dd, J=1.0, 6.0 Hz, 2 H, 2-H$_2$), 4.01 (m$_c$, 2 H, 1'-H$_2$), 5.47 (ttd, J=1.0, 6.5, 15.5 Hz, 1 H, 4-H), 5.64 (ttd, J=1.0, 6.5, 15.5 Hz, 1 H, 3-H).

$^{13}$C NMR (C$_6$D$_6$): δ 3.1 (2q, C-9, -8'), 16.5 (t, C-6), 18.7 (q, 3'-Me), 19.0 (t, C-5'), 29.1 (d, C-3'), 32.2 (t, C-5), 35.2 (t, C-2'), 36.1 (t, C-4'), 38.0 (t, C-2), 62.5 (t, 0-1'), 75.4 (s, C-7'), 75.8 (s, C-8), 78.5 (s, C-7), 79.0 (s, C-6'), 123.3 (d, C-3), 132.6 (d, C-4), 170.8 (s, C-1).

MS: m/z (%) 41 (55) [C$_3$H$_5$$^+$], 53 (76) [C$_4$H$_5$$^+$], 60 (2) [CH$_3$CO$_2$H$^+$], 67 (50) [C$_5$H$_7$$^+$], 81 (100) [C$_6$H$_9$$^+$], 93 (60) [C$_7$H$_9$$^+$], 107 [C$_{10}$H$_{16}$O$_2$$^+$—CO$_2$H], 121 (44) [C$_9$H$_{13}$$^+$], 124 (34) [C$_{10}$H$_{14}$O$_2$$^+$—C$_3$H$_6$], 147 (7) [C$_9$H$_{11}$O$^+$], 207 (1) [M$^+$-C$_5$H$_7$], 259 (1) [M$^+$-CH$_3$], 274 (1) [M$^+$].

C$_{18}$H$_{26}$O$_2$ (274.40): calcd. C 78.79, H 9.55; found C 78.82, H 9.48.

A solution of (3E)-3'-methyloct-6'-ynyl non-3-en-7-ynoate (350 mg, 1.28 mmol) in absolute chlorobenzene (120 mL) was degassed with argon for 15 min, prior to the addition of Schrock's carbyne catalyst (Me$_3$CC≡W(OtBu)$_3$, 60.5 mg, 0.128 mmol). With a slow flow of argon, the resulting mixture was refluxed for 24 h and then allowed to cool down to room temp. The solvent was removed under reduced pressure, and the resulting residue was purified by chromatography on silica gel [50 g; pentane-Et$_2$O (1:1); R$_f$=0.55 in pentane-Et$_2$O (5:1)] to provide (4E)-12-methyloxacyclotetradec-4-en-8-yn-2-one (220 mg, 78%) as a colourless liquid.

IR (neat): ν 1731 (OC=O), 966 (C=C, trans) cm$^{-1}$.

$^1$H NMR (CDCl$_3$): δ 0.90 (d, J=6.5 Hz, 3 H, 12-Me), 1.19 (m$_c$, 1 H, 13-H$_b$), 1.29-1.47 (m, 2 H, 11-H$_b$, 13-H$_a$), 1.68 (m$_c$, 1 H, 11-H$_a$), 2.02 (m$_c$, 1 H, 12-H), 2.13-2.33 (m, 4 H, 7-, 10-H$_2$), 3.00 (ddd, J=1.5, 7.0, 14.0 Hz, 1 H, 6-H$_b$), 3.05 (ddd, J=1.5, 7.0, 14.0 Hz, 1 H, 6-H$_a$), 4.23 (dd, J=4.0, 7.0 Hz, 2 H, 3-H$_2$), 5.56 (ttd, J=1.5, 7.0, 15.0 Hz, 1 H, 5-H), 5.64 (ttd, J=1.5, 7.0, 15.0 Hz, 1 H, 4-H), 7.21-7.36 (m, 2 H, 14-H$_2$).

$^{13}$C NMR (CDCl$_3$): δ 16.0 (t, C-7), 18.1 (t, C-10), 18.5 (q, 12-Me), 25.3 (d, C-12), 31.4 (t, C-6), 34.6 (t, C-13), 35.2 (t, C-11), 39.4 (t, C-3), 61.2 (t, C-14), 79.8 (s, C-9), 80.0 (s, C-8), 123.7 (d, C-4), 132.5 (d, C-5), 171.6 (s, C-2).

MS: m/z (%) 41 (39) [C$_3$H$_5$$^+$], 60 (1) [CH$_3$CO$_2$H$^+$], 99 (2) [C$_7$H$_{15}$$^+$], 160 (2) [M$^+$-O$_2$H$_4$O$_2$], 178 (100) [M$^+$-C$_2$H$_2$O], 205 (1) [M$^+$-CH$_3$], 220 (1) [M$^+$].

Quinoline (27.5 μL, 0.232 mmol) and 10% Pd/BaSO$_4$ (4.90 mg, 0.0461 mmol) were added to a stirred solution of (4E)-12-methyloxacyclotetradec-4-en-8-yn-2-one (256 mg, 1.16 mmol) in ethanol (20 mL). The reaction flask was flushed with argon followed by hydrogen, and the reaction mixture was stirred under hydrogen atmosphere at room temp. and ambient pressure. After 5 h, GC-monitoring indicated complete conversion, upon which the catalyst was filtered off through a pad of Celite and washed with ethanol. The solvent was removed under reduced pressure, and the resulting residue purified by chromatography on silica gel [30 g; pentane-Et$_2$O (20:1); R$_f$=0.60 in pentane-Et$_2$O (5:1)] to furnish (4E, 8Z)-12-methyloxacyclotetradeca-4,8-dien-2-one (223 mg, 86%) as a colourless odoriferous liquid.

IR (neat): ν 1732 (OC=O), 967 (C=C, trans), 714 (C=C, cis) cm$^{-1}$.

$^1$H NMR (C$_6$D$_6$): δ 0.77 (d, J=6.5 Hz, 3 H, 12-Me), 1.07 (dddd, J=3.0, 5.5, 6.5, 10.5 Hz, 1 H, 13-H$_b$), 1.09 (dt, J=6.5, 7.0 Hz, 1 H, 11-H$_b$), 1.28 (dt, J=6.5, 7.0 Hz, 1 H, 11-H$_a$), 1.40 (dddd, J=3.0, 6.5, 9.5, 10.5 Hz, 1 H, 13-H$_a$), 1.48 (ttq, J=6.5, 6.5, 6.5 Hz, 1 H, 12-H), 1.90 (td, J=7.0, 7.0, 2 H, 6-H$_2$), 1.94 (td, J=7.0, 7.5 Hz, 2 H, 10-H$_2$), 1.99 (td, J=7.0, 7.5, 2 H, 7-H$_2$), 2.74 (d, J=6.5 Hz, 2 H, 3-H$_2$), 4.01 (ddd, J=3.0, 9.5, 11.5 Hz, 1 H, 14-H$_{ax}$), 4.10 (ddd, J=3.0, 5.5, 11.5 Hz, 1 H, 14-H$_{eq}$), 5.21 (ttd, J=1.0, 7.5, 11.0 Hz, 1 H, 8-H), 5.31 (ttd, J=1.0, 6.5, 15.5 Hz, 1 H, 4-H), 5.37 (ttd, J=1.0, 7.5, 11.0 Hz, 1 H, 9-H), 5.48 (ttd, J=1.0, 7.0, 15.5 Hz, 1 H, 5-H).

$^{13}$C NMR (C$_6$D$_6$): δ 19.9 (q, 12-Me), 24.9 (t, C-10), 27.9 (t, C-7), 29.1 (d, C-12), 31.8 (t, C-6), 35.3 (t, C-13), 36.7 (C-11), 38.6 (t, C-3), 62.2 (t, C-14), 122.9 (d, C-4), 129.6 (d, C-8), 131.0 (d, C-9), 134.1 (d, C-5), 170.8 (s, C-2).

MS: m/z (%) 41 (41) [C$_3$H$_6$$^+$], 54 (62) [C$_4$H$_6$$^+$], 60 (2) [CH$_3$CO$_2$H$^+$], 67 (58) [C$_5$H$_7$$^+$], 81 (100) [C$_6$H$_9$$^+$], 95 (17), 107 (16) [C$_8$H$_{11}$$^+$], 123 (15) [C$_9$H$_{16}$$^+$], 149 (6) [C$_{11}$H$_{17}$$^+$], 162 (7) [M$^+$-CH$_3$COOH], 194 (1) [M$^+$-CO], 204 (1) [M$^+$-H$_2$O], 222 (2) [M$^+$].

C$_{14}$H$_{22}$O$_2$ (222.33): calc. C 75.63, H 9.97; found C 75.67, H 9.96.

Odour description: powerful warm-metallic, powdery musk odour with herbaceous and floral facets as well as a strong hot-iron inclination.

EXAMPLE 3

Further Compounds

The following compounds may also be prepared following the general procedure described by Example 1 and 2:
(4E,8Z)-13-methyloxacyclopentadeca-4,8-dien-2-one,
(4E,8Z)-14-methyloxacyclohexadeca-4,8-dien-2-one,
(4E,9Z)-12-methyloxacyclotetradeca-4,9-dien-2-one,
(4E,9Z)-14-methyloxacyclohexadeca-4,9-dien-2-one,
(4E,9Z)-15-methyloxacycloheptadeca-4,9-dien-2-one,
(4E,10Z)-13-methyloxacyclo-pentadeca-4,10-dien-2-one,
(4E,10Z)-14-methyloxacyclohexadeca-4,10-dien-2-one,
(4E,10Z)-15-methyloxacycloheptadeca-4,10-dien-2-one,
(4E,11Z)-14-methyloxacyclohexa-deca-4,11-dien-2-one, and
(4E,11Z)-15-methyloxacycloheptadeca-4,11-dien-2-one.

EXAMPLE 4

Feminine Fine Fragrance "Jasmine-White Amber and Green Apple"

| Compound/Ingredient | parts by weight 1/1000 |
|---|---|
| Allyl oenantate (allyl heptanoate) | 17 |
| Amberketal (dodecahydro-3,8,8,11a-tetramethyl-5H-3,5a-epoxynaphth[2,1-c]oxepin) @10%/IPM | 10 |
| Benzyl benzoate (BB) | 131 |
| CASHMERAN ™ (1,2,3,5,6,7-hexahydro-1,1,2,3,3-pentamethyl-4H-inden-4-one) | 80 |
| Cedryl acetate | 40 |
| Citrus peel oil | 130 |
| COSMONE ™ ((5Z)-3-methylcyclotetradec-5-en-1-one) | 20 |
| Cyclal C (2,4-dimetylcyclohex-3-ene carboxaldehyde) | 4 |
| Givescone (ethyl 2-ethyl-6,6-dimethylcyclohex-2-enecarboxylate) | 20 |
| Methyl dihydroisojasmonate (methyl 2-hexyl-3-oxocyclopentanecarboxylate) | 75 |
| Spirambrene (2,2,3',7',7'-pentamethylspiro(1,3-dioxan-5,2'-norcarane)) | 10 |
| Trimofix O (1-(2,6,10-trimethylcyclododeca-2,5,9-trien-1-yl)ethan-1-one) | 10 |
| γ-Undecalactone | 3 |
| Vertofix Coeur (commercial acetyl cedrene fraction) | 350 |
| (4E,9Z)-13-Methyloxacyclopentadeca-4,9-dien-2-one (Example 1) | 100 |

At 10% (4E,9Z)-13-methyloxacyclopentadeca-4,9-dien-2-one (Example 1) conveys to this floral composition around a central *Jasminium sambac* accord a characteristic floral signature musk note, that extends the jasminic theme into a soft-warm, pleasant sweet aromatic-powdery musk foundation with even slightly green-herbaceous aspects that take up the top note green apple impact of Cyclal C. (4E,9Z)-13-Methyloxacyclo-pentadeca-4,9-dien-2-one combines well and intensifies the powdery nitro-musk character of the macrocyclic ketone COSMONE™ and besides boosts the musky aspects of the woody-musky material CASHMERAN™, thereby creating a round and rich signature musk accord in the dry down. Together with Spirambrene and Amberketal, the floral, jasminic musk note of (4E,9Z)-13-methyloxacyclo-pentadeca-4,9-dien-2-one creates a unique "white amber" theme, a transparent white-floral musky ambergris note, which without floral musks such as (4E,9Z)-13-methyloxacyclopentadeca-4,9-dien-2-one could so far not be realized in this lush and lively way.

The invention claimed is:

1. A compound of formula (I)

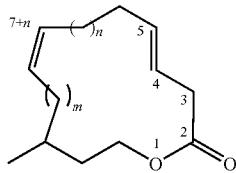

(I)

wherein n and m are independently selected from 1, 2, 3 and 4 with the proviso that 3≦n+m≦6; and
the double bond between C-4 and C-5 is in (E)-configuration and the bond between C-(7+n) and C-(8+n) is in (Z)-configuration.

2. A compound according to claim 1 selected from:
(4E,8Z)-12-methyloxacyclotetradeca-4,8-dien-2-one,
(4E,8Z)-13-methyloxacyclopentadeca-4,8-dien-2-one,
(4E,8Z)-14-methyloxacyclohexadeca-4,8-dien-2-one,
(4E,9Z)-12-methyloxacyclotetradeca-4,9-dien-2-one,
(4E,9Z)-13-methyloxacyclopentadeca-4,9-dien-2-one,
(4E,9Z)-14-methyloxacyclohexadeca-4,9-dien-2-one,
(4E,9Z)-15-methyloxacycloheptadeca-4,9-dien-2-one,
(4E,10Z)-13-methyloxacyclo-pentadeca-4,10-dien-2-one,
(4E,10Z)-14-methyloxacyclohexadeca-4,10-dien-2-one,
(4E,10Z)-15-methyloxacycloheptadeca-4,10-dien-2-one,
(4E,11Z)-14-methyloxacyclohexa-deca-4,11-dien-2-one, and
(4E,11Z)-15-methyloxacycloheptadeca-4,11-dien-2-one.

3. A fragrance compound of formula (I)

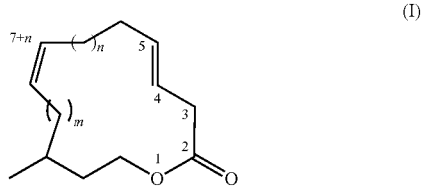

(I)

wherein n and m are independently selected from 1, 2, 3 and 4 with the proviso that 3≦n+m≦6; and
the double bond between C-4 and C-5 is in (E)-configuration and the bond between C-(7+n) and C-(8+n) is in (Z)-configuration, or a mixture thereof.

4. A fragrance application comprising a compound of formula (I) as defined in claim 1, and a consumer product base.

5. A fragrance application according to claim 4 wherein the product base is selected from the group consisting of: fine fragrances, household products, laundry products, body care products and cosmetics.

6. A method of improving, enhancing or modifying a perfume composition or fragrance application, the method comprising the step of: adding thereto an olfactory acceptable amount of a compound of formula (I) as defined in claim 1.

* * * * *